US006372223B1

(12) United States Patent
Kistner et al.

(10) Patent No.: US 6,372,223 B1
(45) Date of Patent: Apr. 16, 2002

(54) INFLUENZA VIRUS VACCINE COMPOSITION

(75) Inventors: Otfried Kistner, Vienna; Noel Barrett, Klosterneuburg/Weidling; Wolfgang Mundt; Friedrich Dorner, both of Vienna, all of (AT)

(73) Assignee: Baxter Aktiengesellschaft, Vienna (AT)

(*) Notice: Subject to any disclaimer, the term of this patent is extended or adjusted under 35 U.S.C. 154(b) by 0 days.

(21) Appl. No.: 09/787,322

(22) PCT Filed: Sep. 14, 1999

(86) PCT No.: PCT/AT99/00223

§ 371 Date: Jun. 12, 2001

§ 102(e) Date: Jun. 12, 2001

(87) PCT Pub. No.: WO00/15251

PCT Pub. Date: Mar. 23, 2000

(30) Foreign Application Priority Data

Sep. 15, 1998 (AT) ............................................. 1555/98

(51) Int. Cl.[7] .......................................... A61K 39/145
(52) U.S. Cl. ............................... 424/209.1; 424/193.1; 424/196.11; 424/210.1; 424/690; 424/682; 435/235.1; 435/236
(58) Field of Search ........................ 424/193.1, 196.11, 424/209.1, 210.1, 278.1, 682, 690; 435/235.1, 236

(56) References Cited

FOREIGN PATENT DOCUMENTS

| WO | WO 96/15231 | 5/1996 |
| WO | WO 97/28809 | 8/1997 |

OTHER PUBLICATIONS

Dillon et al., Induction of Protective Class I MHC–Restricted CTL in Mice By a Recombinant Influenza Vaccine in Aluminum Hydroxide Adjuvant, Vaccine, vol. 10, Issue 5, pp. 309–318, 1992.*
Ionita et al., Archives Roumaines Depathologie Experimentales Et De Microbiologie, 1989 (Jul.–Sep.) 48(3) 265–73.*
Mumford et al., Epidemiology and Infection (Apr.1994) 112(2) 421–37.*
Bachmayer, H.; Split and Subunit Vaccines; *Influenza: Virus, Vaccines, Strategy* (Editor P. Selby); Academic Press, New York; pp. 149–152 (1976).
Coulter, A., et al.; Studies on Experimental Adjuvanted Influenza Vaccines: Comparison of Immune Stimulating Complexes (Iscoms™) and Oil–in Water Vaccines; *Vaccine;* vol. No. 16:11/12; pp. 1243–1253 (1998).
Davenport, F.M., et al.; Lack of Adjuvant Effect of AlPO$_4$ on Purified Influenza Virus Hemagglutinins in Man; *The Journal of Immunology;* vol. 100, No. 5, pp. 1139–1140 (1968).
Fukumi, H.; Effectiveness and Untoward Reactions of Oil Adjuvant Influenza Vaccines; *Symp. Series Immunobiol. Standard;* vol. 6; pp. 237–240 (1967).

Guaraccia, S., et al.; A Comparative Immunogenicity–Reactogenicity Dose–Response Study of Influenza Vaccine; *Annals of Allergy;* vol. 65; pp. 218–221 (Sep. 1990).
Hjorth, R.N., et al.; The Effect of Syntex Adjuvant Formulation (SAF–m) on Humoral Immunity to the Influenza Virus in the Mouse; *Vaccine;* vol. 15:5; pp. 541–546 (1997).
Jennings, R., et al.; Responses of Volunteers to Inactivated Influenza Virus Vaccines; *Journal of Hygiene;* vol. 86:1; pp. 1–16 (1981).
Keitel, W., et al.; Pilot Evaluation of Influenza Virus Vaccine (IVV) Combined with Adjuvant; *Vaccine;* vol. 11:9; pp. 909–913 (1993).
Kistner, O., et al.; Development of a Mammalian Cell (Vero) Derived Candidate Influenza Virus Vaccine; *Vaccine;* vol. 16:9/10; pp. 960–968 (1998).
Kistner, O., et al.; Development of a Vero Cell–Derived Influenza Whole Virus Vaccine; *Dev Biol Stand;* vol. 98; pp. 101–110 (1999).
Martin, J.T.; Development of an Adjuvant to Enhance the Immune Response to Influenza Vaccine in the Elderly; *Biologicals;* vol. 25; pp. 209–213 (1997).
Merten, O.W., et al.; Production of Influenza Virus in Serum–Free Mammalian Cell Cultures; *Dev Biol Stand;* vol. 98; pp. 23–37 (1999).
Nicholson, K.G., et al.; Clinical Studies of Monovalent Inactivated Whole Virus and Subunit A/USSR/77 (H1N1) Vaccine: Serological Responses and Clinical Reactions; *Journal of Biol. Stand.;* vol. 7; pp. 123–136 (1979).
Palache, A.M., et al.; Antibody Response after Influenza Immunization with Various Vaccine Doses: A Doubl–Blind, Placebo–Controlled, Multi–Centre, Dose–Response Study in Elderly Nursing–Home Residents and Young Volunteers; *Vaccine;* vol. 11:1;pp. 3–9 (1993).
Palache, A.M., et al.; Influenza Vaccines: The Effect of Vaccine Dose on Antibody Response in Primed Populations During the Ongoing Interpandemic Period—A Review of the Literature; *Vaccine;* vol. 11:9; pp. 892–908 (1993).
Palmer, D.F., et al.; A Procedural Guide to the Performance of Rubella Hemagglutination–Inhibition Tests; U.S. Dept. of Health, Ed. and Welfare, PHS, Atlanta, GA; pp. 25–62 (1977).
Robuccio, J.A., et al.; Comparison of the Effects of Five Adjuvants on the Antibody Response to Influenza Virus Antigen in Guinea Pigs; *Lab Animal Science;* vol. 45;4; pp. 420–426 (1995).
Skea, D.L., et al.; Adhesion–Mediated Enhancement of the Adjuvant Activity of Alum; *Vaccine;* vol. 11:10; pp. 1018–1026 (1993).
Committee for Proprietary Medicinal Products (CPMP): Note for Guidance on Harmonisation of Requirements for Influenza Vaccines (CPMP/BWP/214/96);pp. 20–21 (1996).

* cited by examiner

Primary Examiner—Laurie Scheiner

(57) ABSTRACT

This invention describes an influenza virus vaccine containing an influenza virus antigen obtained from a cell culture, with an influenza virus antigen content between 1 $\mu$g and 5 $\mu$g per dose and aluminum as an adjuvant as well as a method for its preparation.

8 Claims, No Drawings

INFLUENZA VIRUS VACCINE COMPOSITION

The present invention concerns an influenza virus vaccine composition with a reduced influenza virus antigen content and with aluminum as an adjuvant. In addition, the present invention concerns the use of the vaccine composition in the production of a drug and for the induction of an effective immune response in higher vertebrates, in particular in humans.

Influenza virus infections pose an increasing risk to the health, particularly to the health of the elderly and of persons suffering from chronic diseases, since the infection in these groups of persons frequently leads to an increase in the mortality rate. Since the introduction of an inactive influenza vaccine containing inactive virus material from infected embryonated chicken eggs in the 1940s, the risk and the course of the infection have improved and the mortality rate in the elderly has decreased.

For a vaccine which leads to a positive ratio between the vaccine dose and the IgG antibody response to be effective, health authorities recommend a vaccine dose between 10 $\mu$g and 15 $\mu$g of HA (hemagglutination) antigen per dose.

The short-term production of large quantities of antigen for the manufacture of vaccine during a pandemic, in particular by means of the method using embryonated chicken eggs which has been used so far, is not only labor-intensive and requires a supply of large quantities of eggs but, due to the short intervals of time between identifying the virus type and making the vaccine available, also requires a considerable logistic effort. In addition, due to the increasing awareness that especially the group of people at risk should be vaccinated early on, the future demand for an effective vaccine will increase more and more.

Based on present estimates, the effectiveness of a human influenza virus vaccine is in a range from 30% to 80%. To increase the effectiveness, it has been proposed that the vaccine dose be increased. Studies carried out by Palache et al. (1993, Vaccine 11, pp. 3–9) and Palache et al. (1993, Vaccine 11, pp. 892–908), however, show that an increase in the vaccine dose is not always sufficient to increase the antibody response and to protect those vaccinated since the degree of the antibody response is highly dependent on the antigen. Although it was found that there is a tendency toward an increased immune response if a higher antigen dose is used, this tendency is less pronounced above a range from 10 $\mu$g to 15 $\mu$g and often does not justify the side effects caused by the high vaccine dose.

Other approaches to increasing the immune response, in particular in the elderly, targeted using additional adjuvants. Thus, antigen preparations containing mineral oil emulsions did indeed elicit an immune response that was superior to that of vaccines without this adjuvant; however, they were also responsible for more severe side effects (Fukumi et al., 1967, In: Symposium Series. Immunobiology Standard, Vol. 5, p. 237 ff., Karger, Basel, New York).

In clinical studies involving humans, aluminum, the only adjuvant allowed for use in humans, did not provoke a greater immunogenicity of influenza virus antigen although the immune response in mice had been increased by the adjuvant (Davenport et al., 1968, J. Immunol. 100, pp. 1139–1140, Nicholson et al., 1979, J. Biol. Stand. 7, pp. 123–136, Bachmayr et al., 1976, Split and subunit vaccines. In: Influenza: Virus, Vaccines, Strategy (Ed. P. Selby), Academic Press, New York, pp. 149–152, Jennings et al., 1981, J. Hyg. 81, pp.1–16). Studies carried out by Skea et al. (1993, Vaccine 11, pp. 1018–1026) to examine the increase in the immune response to an influenza virus vaccine also showed that aluminum compounds by themselves are not very effective adjuvants for influenza virus antigen. But Skea et al. (cit. loc.), by increasing the adhesion of HA antigen to aluminium by specific anti-influenza virus HA antibodies, were able to elicit a 1500 times higher immogenicity in mice and a 5 times higher immunogenicity in rabbits compared to aluminum by itself. Based on this, they reasoned that the adjuvant activity of aluminum can be considerably improved by increasing the physical adhesion between the antigen and the adjuvant. So far, data from experiments in higher mammals or humans, however, have not yet been made available.

A number of experiments in which adjuvants with an acceptable reactivity were tested has been carried out. Thus, immunostimulating complexes (ISCOMS™), oil-in-water adjuvants (Coulter et al., 1998, Vaccine 16, pp. 1243–1253), Vaxcel™, TiterMax™, Syntex, $AlPO_4$, Freund's complete and incomplete adjuvant (Robuccio et al., 1995, Lab. Animal Sci. 45, pp. 420–426), poly(amidoamine) dendrimer (WO 97/28809), and MF59 (Keitel et al., 1993, Vaccine 11, pp. 909–913, Martin, 1997, Biologicals 25, pp. 209–213) were tested for their adjuvant activity on influenza virus HA antigen. It was found that the adjuvants used increase the immune response to different degrees. On the other hand, depending on the adjuvant concentration used, they also cause more or less severe side effects.

An additional problem that arises especially when groups of high-risk individuals, such as persons suffering from allergies and patients with asthma, are vaccinated with the conventional influenza virus vaccine from chicken eggs relates to the fact that these individuals are particularly prone to developing side effects, such as allergic reactions to chicken proteins. In many cases, even a small quantity of chicken protein was enough to provoke life-threatening, hypersensitive, allergic reactions. As a result, it became the general practice to dilute the influenza virus vaccine at a ratio of 1:10 to reduce the quantity of chicken protein that was administered along with the vaccine. Studies carried out by Guarnaccia et al. (1990, Ann. Allergy 65, pp. 218–221), however, showed that the reduction of the normally administered quantity of influenza virus antigen also leads to a considerable reduction of the immune response and therefore recommended that quantity of antigen not be reduced since such a reduction fails to ensure an adequate protection of the patients against a viral infection.

Thus, the problem to be solved by the present invention is to make available a vaccine composition which does not have the disadvantages described above, such as high antigen dose, adjuvants which provoke side effects, or allergic reactions to chicken proteins.

This problem is solved according to the present invention by making available an influenza virus vaccine containing influenza virus antigen obtained from a cell culture, with a maximum of 1 $\mu$g to 5 $\mu$g of influenza virus antigen per dose and with aluminum as an adjuvant.

In corroboration of the results obtained by Guarnaccia et al. (1990, Ann. Allergy 65, pp. 218–221) it was found that a reduction of the influenza antigen quantity in a vaccine dose also leads to a decreased immune response in mice. Also, in agreement with the results obtained by Davenport et al. (1968, J. Immunol. 100, pp. 1139–1140, Hjorth et a., 1997, Vaccine 15, pp. 541–546), it was possible to show that with a vaccine composition which contains influenza virus antigen that has been isolated by conventional means from infected embryonated chicken eggs and, at the same time, aluminum as an adjuvant, the HA titer is increased. But with a vaccine dose with a content of antigen that has been reduced to as much as 1/10 of the normally adequate antigen dose (1.5 μg), the addition of aluminum led to an HA titer that is approximately as high as the vaccine containing 10 times the quantity of antigen (Table 1).

Surprisingly, however, it was found that the same quantity of an antigen of the same influenza virus strain that was isolated from a cell culture infected with influenza virus induced 2 times as high an antibody titer as the antigen that is isolated from chicken eggs. In addition, it was possible to show that the addition of aluminum to a preparation containing antigen that has been isolated from a cell culture increases the immune response of the antigen only insignificantly, if at all, when a normally high antigen dose is administered, whereas during an immunization with a preparation that contains a considerably lower dose of this antigen and aluminum as an adjuvant, the HA titer is even higher than that of a higher antigen dose (Table 1) and thus leads to an increased immune response.

Therefore, the adjuvant activity of aluminum for influenza virus antigen that has been isolated from a cell culture is considerably higher than for an antigen that has been isolated from embryonated eggs. This was all the more surprising in that it was generally known to those skilled in the art that at an antigen content of $\leq 10$ μg of antigen per dose, the immune response is considerably reduced (Guarnaccia et al., 1990, Ann. Allergy 65, pp. 218–221) and that aluminum has only a week adjuvant effect on influenza antigen.

In addition, it could not have been foreseen that especially an influenza virus antigen preparation, which had been produced from purified antigen from a cell culture, and the combination of a reduced influenza virus antigen content and aluminum as an adjuvant would lead to a considerably higher immune response than that that can be obtained with a preparation with a content of $\geq 10$ μg of antigen per dose without adjuvant. As a result of the reduction of the antigen content in the vaccine and the presence of aluminum as an adjuvant, it was possible to obtain a 10-fold increase in the immunogenicity of the influenza virus antigen that had been isolated from the cell culture.

According to a special aspect of the present invention, the influenza virus vaccine according to the present invention contains 1 μg to 2.5 μg of antigen per dose. Especially recommended is a vaccine formulation according to the present invention with an influenza virus antigen content of 1.5 pg per dose.

The influenza virus vaccine according to the present invention contains aluminum, preferably in the form of aluminum hydroxide ($Al(OH)_3$) or aluminum phosphate ($AlPO_4$). In the vaccine formulation, the concentration of aluminum can preferably reach a final strength of 0.05% to 0.5%.

In addition to the increased immunogenicity of the preparation, the special advantage of the vaccine formulation according to the present invention is to be seen in the fact that, as a result of (i) the reduced antigen content and (ii) the use of an adjuvant which has been tested over many years and which has already been approved for use in humans, it is nearly completely free from side effects.

In addition, from an antigen quantity normally required for one dose of vaccine, it is possible to produce up to 10 times as many doses of vaccine (15 μg per dose vs. 1.5 μg per dose). As a result, not only the industrial expenditure required in the production of the antigen is reduced but at the same time, it is possible to solve the problems which may arise if a pandemic were to break out, namely of rapidly making available several million doses of vaccine.

In the context of the present invention, it was not only possible to show that the vaccine according to the present invention induces an improved immune response in mice but experiments with chimpanzees also showed that the vaccine preparation according to the present invention is effective in higher mammals as well. This was especially surprising since it was not to be expected that (i) the immunoadsorbent, i.e., aluminum, would have the effect of improving the immune response in higher mammals and that (ii) the reduction of the antigen content would provoke a considerably higher immune response in chimpanzees. At the same time, these experiments also showed that the preparation according to the present invention is nearly completely free from any side effects.

In particular, it was found that the purified influenza virus antigen preparation which was obtained from the cell culture does not only fulfill all of the criteria listed in the CPMP guidelines which must be met by all effective virus vaccines but also that the antigen in the vaccine, compared to a conventional vaccine from eggs, has a considerably higher immunogenicity and, in addition, does not contain chicken proteins which are responsible for potential allergic reactions.

The experiments also show that the increase in the HA titer in chimpanzees which had been immunized with influenza virus antigen isolated from a cell culture was not only considerably higher than in animals which had been immunized with the conventional vaccine with the same dose of antigen but also that the immune response after immunization with a vaccine with a lower quantity of antigen (1–5 μg of antigen per dose) and an adjuvant . . . [ungrammatical sentence or text missing] . . . after 90 days, the HA titer was in part one third higher than or twice as high as when a higher quantity of antigen without an adjuvant was administered (Table 4).

According to a special aspect of the present invention, the vaccine according to the present invention preferably contains influenza virus antigen which is produced and isolated from a cell culture that has been infected with influenza virus. The cell culture can be a Vero cell culture that has been cultivated in a serum- or protein-free medium, with the influenza virus antigen preferably being obtained according to the method described in the International Patent No. WO 96/15231. After purification by means of continuous density-gradient centrifugation and DNase treatment, a solution containing influenza virus that has been obtained using this particular method is obtained in the form of a purified, concentrated virus antigen preparation. This concentrated preparation can be used in the subsequent production of the vaccine according to the present invention.

Another aspect of this invention relates to a method for the production of an influenza virus vaccine for higher mammals, in particular for humans, which comprises the following steps infecting a cell culture with influenza virus cultivating the infected cells harvesting the viruses produced purifying the virus preparation producing a concentrated virus preparation diluting the virus preparation to an antigen content between 1 μg to 5 μg of antigen per dose and adding aluminum as an adjuvant in a concentration between 0.05% to 0.5%.

The production of the influenza virus antigen for the vaccine is preferably carried out in a serum- or protein-free cultivated Vero cell culture as described in International Patent No. WO 96/15231. The cells infected with influenza virus are cultivated until the desired virus titer is obtained, and the viruses are isolated from the supernatant portion of the culture. It was found that the purification of the virus preparations obtained is especially important. In this context, one purification method has proved to be especially suitable; it comprises the steps of a saccharose gradient DNase treatment, and diafiltration and sterile filtration. Even after the preparation that has been purified according to this method is diluted to 1/10 of the antigen content administered in one conventional dose of vaccine and aluminum as an adjuvant is added, it still provokes an immune response that is higher than the vaccine preparation containing no adjuvant but an antigen content of 15 µg of antigen per dose which had normally been considered necessary to be effective.

Another aspect of the present invention relates to the use of an influenza virus preparation with a maximum antigen content between 1 µg to 5 µg of antigen per dose and with aluminum as an adjuvant for the prophylaxis against influenza virus infections.

In this context, the use according to the present invention to prevent an influenza virus infection in humans is to be especially preferred. Since, due to the absence of egg-specific proteins, the probability of an allergic reaction to these proteins is excluded, the vaccine according to the present invention is especially suitable for administration to groups of persons who are high-risk individuals, such as asthmatics and allergy sufferers, as well as to individuals with an immunodeficiency and to the elderly.

Based on the tests on chimpanzees carried out in the context of the present invention, it was found that especially the influenza virus antigen which had been obtained from a cell culture and to which aluminum as an adjuvant had been added induces a better immune response and thus is a better immunogen than an antigen that has been prepared by means of conventional methods. Furthermore, the vaccine according to the present invention has the advantage that it is available in a form free from chicken protein and therefore does not have the side effects generally connected with this protein.

This invention will be explained in greater detail on the basis of the following examples. The tables show:

Table 1: HA titer of pooled mouse sera following a vaccination with influenza A or B virus preparations which had been obtained from infected cell cultures or embryonated eggs.

Table 2: Seroconversion in chimpanzees following immunization with different influenza virus vaccine preparations.

Table 3: Geometric mean of the HA titer (GMT) in chimpanzees following immunization with different influenza virus vaccine preparations.

Table 4: Increase in the GMT in chimpanzees following immunization with various influenza virus vaccine preparations.

Table 5: Protective titer in chimpanzees following immunization with different influenza virus vaccine preparations.

EXAMPLES

Example 1

Production of an Influenza Virus Vaccine Preparation

The influenza virus was obtained from a protein-free Vero cell culture that had been infected with an influenza A or B virus strain according to International Patent No. WO 96/15231 or from allantois liquor of infected embryonated chicken eggs.

To produce an influenza virus preparation from a cell culture, the supernatant liquid of an infected Vero cell culture was mixed with formalin (final strength 0.025%), and the viruses were inactivated for 24 h at 32° C. This material was purified by means of zonal centrifugation in a continuous 0–50% sacharose gradient, DNase treatment, diafiltration, and sterile filtration. The purified material was stored at −70° C.

The final product was tested for residual contaminants, and the following criteria were determined for each dose:

| | |
|---|---|
| Hemagglutinin content: | $\geq 15$ µg of HA per strain |
| Protein content: | $\leq 250$ µg |
| Saccharose content: | $\leq 200$ µg |
| Formalin content: | $\leq 5$ µg |
| Benzonase content: | $\leq 5$ ng |
| Residual DNA (Vero): | $\leq 100$ pg |
| Endotoxin content: | $\leq 100$ EU |
| Pyrogen: | Free |

Example 2

Influence of Al(OH)$_3$ on the Immunogenicity of Different Influenza Virus Vaccine Preparations The isolated antigen preparations of example 1 were diluted in PBS to obtain an HA antigen content of 15 µg/mL, and optionally Al(OH)$_3$ was added as an adjuvant to reach a final strength of 0.2%. To produce a vaccine preparation of 1.5 µg, the solution was appropriately diluted with PBS containing Al(OH)$_3$.

In each case, 10 mice were immunized with 1 mL of the appropriate preparation of, respectively, 15 µg or 1.5 µg of influenza virus HA antigen, both with and without Al(OH)$_3$ as an adjuvant. After 4 weeks, blood was drawn from the mice, and subsequently the mice received booster shots. Two weeks after the booster shot, the animals were exsanguinated. Using the influenza A and B virus hemagglutination test (HAI titer) according to the method described by Palmer et al. (1977, Advanced laboratory technicals for immunological diagnostic, U.S. Dept. Health Ed. Welfare. P. H. S. Atlanta, Immunology Ser. No. 2, A Procedural Guide to the Performance of Rubella Hemagglutination Inhibition Tests, pp. 3–64), the serum obtained was tested.

In Table 1, the results of the experiment with the influenza A virus strain Johannesburg (A/H3N2) preparation and the influenza B virus strain B/Harbin preparation from the Vero cell culture and NIB-34 (HG Johannesburg) from allantois liquor are listed. The serum of the individual mice within each group was pooled after 4 and again after 6 weeks, and the antibody titer was determined using the HAI test.

Both with the lower and the higher antigen dose, the addition of Al(OH)$_3$ as an adjuvant led to a higher increase in titer. The lower dose of 1.5 µg of HA antigen with Al(OH)$_3$ as an adjuvant resulted in an equally high titer as the higher dose containing 15 µg of antigen.

Six weeks after the immunization, the mice which had been vaccinated with a vaccine preparation which had obtained from a cell culture and which contained the higher antigen dose of 15 µg, both with and without adjuvant, showed the same titer. The preparation containing the antigen dose of 1.5 µg, which was ten times lower, plus Al(OH)$_3$ led to a considerably higher HA titer when compared not only to the antigen without adjuvant but also to the higher antigen dose with adjuvant. In the preparation containing the higher dose of antigen which had been isolated from a cell culture, aluminum did not have the effect of improving the immune response. As to the preparation isolated from allantois liquor, 6 weeks after the immunization, Al(OH)$_3$ had only an insignificant influence on the immune response whereas an increase in the titer was determined with the vaccine with a low antigen dose to which an adjuvant had been added.

Thus, in agreement with the results obtained by Davenport et al. (1968, J. Immunol. 100, pp. 1139–1140), the data show that aluminum has the effect of increasing the immune response of mice to influenza antigen from allantois liquor.

It had, however, not been expected that by reducing the antigen concentration to $\frac{1}{10}$ of the "normal" dose and by adding Al(OH)$_3$, the immune response would be equally high as that obtained with the 10 times higher dose and/or that after immunization with antigen obtained from a cell culture, the titer would increase even above that obtained with the higher antigen dose containing Al(OH)$_3$.

TABLE 1

HA titer of pooled mouse sera after vaccination with influenza A or B virus preparations obtained from a cell culture or from embryonated eggs

| | | | | | HAI titer | |
| --- | --- | --- | --- | --- | --- | --- |
| Group | Antigen | Origin | Dose (μg) | Adjuvant | 4 Weeks | 6 Weeks |
| A | A/Johannesburg | VERO | 15 | | 320 | 1280 |
| B | A/Johannesburg | VERO | 1.5 | | 160 | 320 |
| C | A/Johannesburg | VERO | 15 | Al(OH)$_3$ | 640 | 1280 |
| D | A/Johannesburg | VERO | 1.5 | Al(OH)$_3$ | 640 | 2560 |
| E | B/Harbin | VERO | 15 | | n.b.* | 320 |
| F | B/Harbin | VERO | 1.5 | | n.b. | 160 |
| G | B/Harbin | VERO | 15 | Al(OH)$_3$ | n.b. | 320 |
| K | B/Harbin | VERO | 1.5 | Al(OH)$_3$ | n.b. | 640 |
| I | NIB 34 | Allantois | 15 | | 160 | 640 |
| J | NIB 34 | Allantois | 1.5 | | 160 | 320 |
| K | NIB 34 | Allantois | 15 | Al(OH)$_3$ | 640 | 1280 |
| L | NIB 34 | Allantois | 1.5 | Al(OH)$_3$ | 640 | 1280 |

*n.b. = not determined

Example 3
Testing the Long-term Immunity of Chimpanzees Following an Administration of Influenza Virus Vaccine The results of Example 2 show a dramatic increase in the immune response in mice following immunization with a vaccine preparation with a reduced antigen content and with Al(OH)$_3$ as an adjuvant. For this reason, additional studies were carried out to investigate whether this effect can also be observed in higher mammals. To this effect, a long-term study on chimpanzees was carried out.

The study of long-term immunity of chimpanzees following the administration of an influenza whole virus vaccine was carried out using 4 groups of a total of 44 chimpanzees.

The groups were immunized according to the following pattern:

Group I: 13 chimpanzees were immunized with an influenza vaccine preparation from a Vero cell culture with 15 μg per strain.

Group II: 5 chimpanzees were immunized with an influenza vaccine preparation from a Vero cell culture with 5 μg per strain and Al(OH)$_3$ as an adjuvant.

Group III: 13 chimpanzees were immunized with an influenza vaccine preparation from a Vero cell culture with 1.5 μg per strain and Al(OH)$_3$ as an adjuvant.

Group IV: 13 chimpanzees were immunized with an influenza vaccine preparation obtained from the allantois liquor of embryonated eggs with 15 μg per strain.

After 0, 10, 30, and 90 days following the vaccination, the blood of the 44 chimpanzees was sampled. After an RDE (receptor destroying enzyme) treatment, the sera of the chimpanzees were inactivated for 45 min at 56° C. and tested for anti-hemagglutination antibodies against influenza virus wild type strain Texas-36 (A/H1N1), Nanchang (A/H3N2), and B/Harbin (B) by means of the hemagglutination test. The interpretation followed the CPMP guidelines (Committee for Proprietary Medicinal Products (CPMP): Note for Guidance on Harmonization of Requirements for Influenza Vaccines (CPMP/BWP/214/96), Jul. 17, 1996, pp. 20–21). According to these guidelines, an effective vaccine has to meet a minimum of one of the following criteria:

Percent of the seroconversion or a significant increase in the anti-hemagglutination titer ($\geq$40) (Table 2) to >40%.

Increase in the GMT (geometric mean titer) by >2.5 (Tables 3 and 4).

The percentage of subjects who reach an HAI titer of $\geq$40 (protective titer) should be >70% (Table 5).

The results are summarized in Tables 2 through 5 and show that, like the conventional vaccine obtained from an allantois liquor, the influenza virus preparation obtained from a Vero cell culture meets all three criteria demanded by the CPMP guidelines. The vaccine preparation obtained from a Vero cell culture therefore is not only as immunogenic as that obtained from the allantois liquor but, based on the data, it also has a higher immunogenicity.

Surprisingly, it was also discovered that a preparation which has been produced from a Vero cell culture and which has been diluted in a ratio of 1:3 (5 μg per strain) or 1:10 (1.5 μg per strain) and to which Al(OH)$_3$ has been added as an adjuvant also meets all 3 of the criteria beginning on day 30 and 90, respectively, following the immunization.

Thus, in particular Table 2 shows that 30 days after immunization, the chimpanzees that had been vaccinated with a purified influenza virus vaccine preparation obtained from a cell culture had a higher seroconversion compared to those chimpanzees which had been vaccinated with a conventionally produced vaccine obtained from allantois liquor. It was especially surprising to discover that the seroconversion was highest for the preparation with a low antigen dose (5 μg and 1.5 μg) and containing Al(OH)$_3$ as an adjuvant.

The tendency for the immune response in chimpanzees that have been immunized with a vaccine preparation with a low antigen dose and an aluminum compound as an adjuvant to be higher than in those animals that had been given a "normally" high antigen dose without an adjuvant is also corroborated by the increase in the HA titer (Tables 3 and 4). Thus, after 30 days, it is possible to identify an increase in the HA titer for the influenza virus antigen that was isolated from a cell culture that is twice as high as that obtained with the antigen from allantois liquor, and this effect is even more obvious with a low antigen dose containing an adjuvant (Table 4). Ninety days after immunization, the increase in the GMT for the purified vaccine preparation that was produced from a cell culture was nearly twice as high as that observed with the conventional vaccine.

Comparisons of the immunogenicity obtained with influenza virus antigen preparations isolated from the allantois liquor of embryonated eggs and those isolated from a Vero cell culture showed that the antigen isolated from a cell culture has an immunogenicity that is 2 to 4 times higher than the antigen isolated from an allantois liquor.

TABLE 2

Seroconversion of chimpanzees following immunization with different influenza virus vaccine preparations % with a 4-fold or higher HI titer increase
Strain

| | Day | Texas-36 | Nanchang | B/Harbin |
|---|---|---|---|---|
| Group I | | | | |
| Vero cell material 15 µg/strain | 10 | 69% (9/13) | 69% (9/13) | 62% (8/13) |
| | 30 | 85% (11/13) | 77% (10/13) | 85% (11/13) |
| | 90 | 69% (9/13) | 69% (9/13) | 85% (11/13) |
| Group II | | | | |
| Vero cell material 5 µg strain (Al(OH)$_3$) | 10 | 60% ( /5) | 60% (3/5) | 60% (3/5) |
| | 30 | 100% (5/5) | 80% (4/5) | 100% (5/5) |
| | 90 | 80% (4/5) | 80% (4/5) | 100% (5/5) |
| Group III | | | | |
| Vero cell material 1.5 µg strain (Al(OH)$_3$) | 10 | 54% (7/13) | 69% (9/13) | 46% (6/13) |
| | 30 | 92% (12/13) | 92% (12/13) | 85% (11/13) |
| | 90 | 85% (11/13) | 85% (11/13) | 77% (10/13) |
| Group IV | | | | |
| Antigen from eggs 15 µg strain | 10 | 46% (6/13) | 54% (7/13) | 62% (8/13) |
| | 30 | 69% (9/13) | 69% (9/13) | 77% (10/13) |
| | 90 | 67% (8/12) | 67% (8/12) | 83% (10/12) |
| CPMP criteria for effectiveness | | >40% | >40% | >40% |

TABLE 3

Geometric mean of the HA titer (GMT) of chimpanzees following immunization with different influenza virus vaccine preparations GMT (Geometric mean titer)
Strain

| | Day | Texas-36 | Nanchang | B/Harbin |
|---|---|---|---|---|
| Group I–IV | 0 | 21.6 | 11.0 | 7.5 |
| Group I | | | | |
| Vero cell material 15 µg strain | 0 | 21.1 | 10.0 | 7.3 |
| | 10 | 80.0 | 36.0 | 22.3 |
| | 30 | 168.8 | 84.0 | 58.1 |
| | 90 | 52.2 | 49.5 | 42.2 |
| Group II | | | | |
| Vero cell material 5 µg strain (Al(OH)$_3$) | 0 | 17.4 | 10.0 | 6.6 |
| | 10 | 52.8 | 30.3 | 13.2 |
| | 30 | 160.0 | 69.6 | 46.0 |
| | 90 | 69.6 | 60.6 | 46.0 |
| Group III | | | | |
| Vero cell material 1.5 µg strain (Al(OH)$_3$) | 0 | 18.0 | 10.6 | 7.3 |
| | 10 | 40.0 | 44.5 | 14.1 |
| | 30 | 208.9 | 104.4 | 64.6 |
| | 90 | 80.0 | 71.9 | 55.1 |
| Group IV | | | | |
| Antigen from eggs 15 µg strain | 0 | 29.1 | 13.1 | 8.5 |
| | 10 | 64.6 | 34.1 | 22.3 |
| | 30 | 160.0 | 64.6 | 58.1 |
| | 90 | 84.8 | 59.9 | 44.3 |

TABLE 4

Increase in the GMT in chimpanzees following immunization with various influenza virus vaccine preparations Increase in the GMT (prior to/after the vaccination)
Strain

| | Day | Texas-36 | Nanchang | B/Harbin |
|---|---|---|---|---|
| Group I | | | | |
| Vero cell material 15 µg strain | 10 | 3.8 | 3.6 | 3.1 |
| | 30 | 8.0 | 8.4 | 8.0 |
| | 90 | 2.5 | 5.0 | 5.9 |
| Group II | | | | |
| Vero cell material 5 µg strain (Al(OH)$_3$) | 10 | 3.0 | 3.0 | 2.0 |
| | 30 | 9.2 | 7.0 | 7.0 |
| | 90 | 4.0 | 6.1 | 7.0 |
| Group III | | | | |
| Vero cell material 1.5 µg strain (Al(OH)$_3$) | 10 | 2.2 | 4.2 | 1.9 |
| | 30 | 11.6 | 9.9 | 8.9 |
| | 90 | 4.4 | 6.8 | 7.6 |
| Group IV | | | | |
| Antigen from eggs 15 µg strain | 10 | 2.2 | 2.6 | 2.6 |
| | 30 | 5.5 | 4.9 | 6.8 |
| | 90 | 2.9 | 4.6 | 5.1 |
| CPMP criteria for effectiveness | | >2.5 | >2.5 | >2.5 |

TABLE 5

Protective titer of chimpanzees after immunization with different influenza virus vaccine preparations % with HI titer >40
Strain

| | Day | Texas-36 | Nanchang | B/Harbin |
|---|---|---|---|---|
| Group I–IV | 0 | 25% (11/44) | 21% (9/44) | 14% (6/44) |
| Group I | | | | |
| Vero cell material 15 µg strain | 0 | 23% (3/13) | 15% (2/13) | 15% (2/13) |
| | 10 | 92% (12/13) | 85% (11/13) | 39% (5/13) |
| | 30 | 100% (13/13) | 92% (12/13) | 100% (13/13) |
| | 90 | 92% (12/13) | 85% (11/13) | 85% (11/13) |
| Group II | | | | |
| Vero cell material 5 µg strain (Al(OH)$_3$) | 0 | 20% (1/5) | 20% (1/5) | 0% (0/5) |
| | 10 | 80% (4/5) | 80% (4/5) | 20% (1/5) |
| | 30 | 100% (5/5) | 100% (5/5) | 100% (5/5) |
| | 90 | 100% (5/5) | 100% (5/5) | 100% (5/5) |
| Group III | | | | |
| Vero cell material 1.5 µg strain (Al(OH)$_3$) | 0 | 15% (2/13) | 15% (2/13) | 15% (2/13) |
| | 10 | 69% (9/13) | 69% (9/13) | 23% (3/13) |
| | 30 | 100% (13/13) | 100% (13/13) | 100% (13/13) |
| | 90 | 100% (13/13) | 100% (13/13) | 92% (2/13) |
| Group IV | | | | |
| Antigen from eggs 15 µg strain | 0 | 39% (5/13) | 31% (4/13) | 15% (2/13) |
| | 10 | 85% (11/13) | 77% (10/13) | 46% (6/13) |
| | 30 | 100% (13/13) | 100% (13/13) | 92% (12/13) |
| | 90 | 100% (12/12) | 83% (10/12) | 92% (11/12) |
| CPMP criteria for effectiveness | | >70% | >70% | >70% |

What is claimed is:

1. An influenza virus vaccine comprising an influenza virus antigen isolated from a cell culture and having an influenza virus antigen content between 1 µg and 5 µg/dose and with aluminum as an adjuvant.

2. The influenza virus vaccine of claim 1, having an antigen content of 1 µg to 2.5 µg per dose.

3. The influenza virus vaccine of claim 1 wherein said aluminum is aluminum hydroxide or aluminum phosphate.

4. The influenza virus vaccine of claim 1, which comprises aluminum in a final strength of 0.05% to 0.5%.

5. The influenza virus vaccine of claim 1, which comprises a purified influenza virus antigen.

6. A method for the preparation of an influenza virus vaccine, comprising the following steps infecting a cell culture with influenza virus cultivating the infected cells harvesting the viruses produced purifying the virus preparation producing a concentrated virus preparation diluting the virus preparation to an antigen content between 1 µg to 5 µg per dose and adding aluminum as an adjuvant in a concentration between 0.05% to 0.5%.

7. A method of immunizing against influenza virus in a mammal which comprises administering the influenza virus vaccine of claim 1.

8. The method of claim 7, wherein said mammal is a human.

* * * * *